(12) United States Patent
Eyre et al.

(10) Patent No.: US 7,864,919 B1
(45) Date of Patent: *Jan. 4, 2011

(54) NONDESTRUCTIVE METHOD OF MEASURING A REGION WITHIN AN ULTRA-HARD POLYCRYSTALLINE CONSTRUCTION

(75) Inventors: Ronald K. Eyre, Orem, UT (US); Terry Lee Woodruff, Ponca City, OK (US); Loel Gene Corbett, Saratoga Springs, UT (US)

(73) Assignee: Smith International, Inc., Houston, TX (US)

( * ) Notice: Subject to any disclaimer, the term of this patent is extended or adjusted under 35 U.S.C. 154(b) by 1081 days.

This patent is subject to a terminal disclaimer.

(21) Appl. No.: 11/550,671

(22) Filed: Oct. 18, 2006

Related U.S. Application Data

(60) Provisional application No. 60/728,057, filed on Oct. 18, 2005.

(51) Int. Cl.
*G01N 23/223* (2006.01)
(52) U.S. Cl. ......................................... 378/44
(58) Field of Classification Search .................. 378/44, 378/50
See application file for complete search history.

(56) References Cited

U.S. PATENT DOCUMENTS

| | | | |
|---|---|---|---|
| 5,603,414 A | 2/1997 | Rooney et al. | |
| 5,835,205 A | 11/1998 | Hunter et al. | |
| 6,544,308 B2 | 4/2003 | Griffin et al. | |
| 7,196,782 B2 | 3/2007 | Fielden et al. | |
| 7,302,034 B2 * | 11/2007 | Grodzins | 378/50 |
| 7,616,734 B1 * | 11/2009 | Corbett et al. | 378/46 |
| 2009/0139150 A1 | 6/2009 | Ras | |

* cited by examiner

*Primary Examiner*—Jurie Yun
(74) *Attorney, Agent, or Firm*—Connolly Bove Lodge & Hutz LLP

(57) ABSTRACT

A method for determining a position of a region within an ultra-hard polycrystalline body comprises directing x-rays onto the body, wherein the body includes one region that includes a target atom and another region that does not. The ultra-hard polycrystalline body can be in the form of a cutting element used with a subterranean drill bit. The x-rays penetrate the body and cause the target atom within the region including the same to emit x-ray fluorescence. The emitted x-ray fluorescence is received and the position of the second region within the body is determined therefrom. In one embodiment, the one region extends a depth from the surface, and the other region extends from one region into the body. The x-rays can be directed onto a number of different body surface portions to determine the placement position of the region comprising the target atom within the polycrystalline body.

25 Claims, 6 Drawing Sheets

NONDESTRUCTIVE METHOD OF MEASURING A REGION WITHIN AN ULTRA-HARD POLYCRYSTALLINE CONSTRUCTION

RELATION TO COPENDING PATENT APPLICATIONS

This patent application claims priority of U.S. Provisional Patent Application Ser. No. 60/728,057, that was filed on Oct. 18, 2005, and which is incorporated herein by reference.

FIELD OF THE INVENTION

This invention relates to nondestructive methods developed for measuring the thickness or variation in thickness of a region within a material microstructure and, more specifically, to using X-ray fluorescence as a technique for measuring the thickness or variation in thickness of one or more region within an ultra-hard polycrystalline construction.

BACKGROUND OF THE INVENTION

The formation of constructions having a material microstructure made up or two or more different layers or regions of materials is well known. Such constructions are intentionally engineered in this fashion to provide a desired mix of physical, mechanical and/or thermal properties within the material microstructure, making it better equipped to handle a particular end use application. In order to provide such desired properties in a predictable and consistent manner, the thickness or variation of thickness of each engineered region must be controlled.

It is, therefore, necessary that the thickness of each such region within the construction be measured for the purpose of both controlling the process that is used to make the construction, and for controlling the quality or ability of the construction to perform as expected. Methods useful for measuring the thickness or variation in the thickness of a region within a material construction will vary depending on the nature of the construction. For material constructions used in tooling, wear, and cutting applications provided in the form of an ultra-hard polycrystalline material, e.g., comprising polycrystalline diamond, a useful method for measuring the thickness or variation of thickness of one or more region within the construction is by destructive method or destructive testing.

Destructive testing requires that the construction itself be cut or otherwise treated in a manner that physically exposes the different regions therein so that they can be measured by visual inspection. In an example embodiment, where the construction is one comprising an ultra-hard polycrystalline material such as diamond or cubic boron nitride, the construction itself is cut, e.g., in half, so that the different regions forming the construction can be viewed visually for purposes of measuring the thickness or variation of thickness of the regions. In an example embodiment, such visual indication is made with the assistance of a magnifying device such as a microscope, e.g., a scanning electron microscope.

While such destructive test method is useful for determining the thickness or variation of thickness within a construction, it is time consuming in that after the part is cut it must usually be further prepared by grinding, polishing or the like, then mounted for microscopic evaluation, and the microscopic evaluation must be taken over a number of different points to gather sufficient data to arrive at a numerical value, e.g., an average region thickness throughout the part. Further, the use of such destructive test method is expensive, and results in the parts that are measured being destroyed, thereby adversely impacting the economics of making the parts.

It is, therefore, desired that a method be developed that is capable of measuring the thickness or variation of thickness within a region of a material construction, e.g., an ultra-hard polycrystalline construction, in a manner that is not destructive. It is further desired that such a method be capable of providing such a desired measurement in a manner that has a consistent degree of accuracy. It is further desired that the method be capable of providing such a desired measurement for products where the region being measured may have a nonplanar or nonlinear configuration.

SUMMARY OF THE INVENTION

Methods of this invention are disclosed for determining a position of a region within an ultra-hard polycrystalline body. The ultra-hard polycrystalline body can be provided in the form of a cutting element, wherein the body is attached to a suitable substrate, and the cutting element is configured for attachment and use with a bit, e.g., for drilling subterranean earthen formations. The method comprises using a suitable device to direct x-rays onto at least a surface portion of the polycrystalline body.

The polycrystalline body comprises more than one region, and in an example embodiment, comprises a first region and a second region. In a preferred embodiment, the first and second regions each comprise bonded together diamond crystals. One of the regions includes a target atom that is selected so that it emits x-ray fluorescence in response to receiving x-ray radiation. In an example embodiment, the first region does not include the target atom, and the second region includes the target atom. The target atom can be a catalyst material used to form polycrystalline diamond, such as cobalt and the like.

When the x-rays are directed onto the body they reach the second region, and the target atoms in the second region emit x-ray fluorescence. The emitted x-ray fluorescence is received and the position of the second region within the body is determined therefrom. In an example embodiment, the first region extends a depth from the surface, and the second region extends from the first region a depth into the body. If desired, x-rays can directed onto a number of different surface portions of the body to determine the placement position, e.g., depth and/or thickness, of the region comprising the target atom within the polycrystalline body.

Methods of this invention are, therefore capable of measuring the placement position, thickness or variation of thickness within a region of a material construction, e.g., an ultra-hard polycrystalline construction, in a manner that is not destructive, and that has a consistent degree of accuracy. Further, methods this invention can be used to determine such placement position where the region being measured may have a nonplanar or nonlinear configuration.

BRIEF DESCRIPTION OF THE DRAWINGS

These and other features and advantages of the present invention will be appreciated as the same becomes better understood by reference to the following detailed description when considered in connection with the accompanying drawings wherein.

DETAILED DESCRIPTION OF THE INVENTION

A nondestructive method useful for determining the thickness or variation of thickness within an ultra-hard polycrystalline construction, according to the principles of this invention, is X-ray fluorescence (XRF). As described in better detail below, XRF is used to determine the thickness and/or variation in thickness within a targeted region of the ultra-hard polycrystalline construction in a manner that is accurate and that does not result in the destruction of the part.

Figure 1:
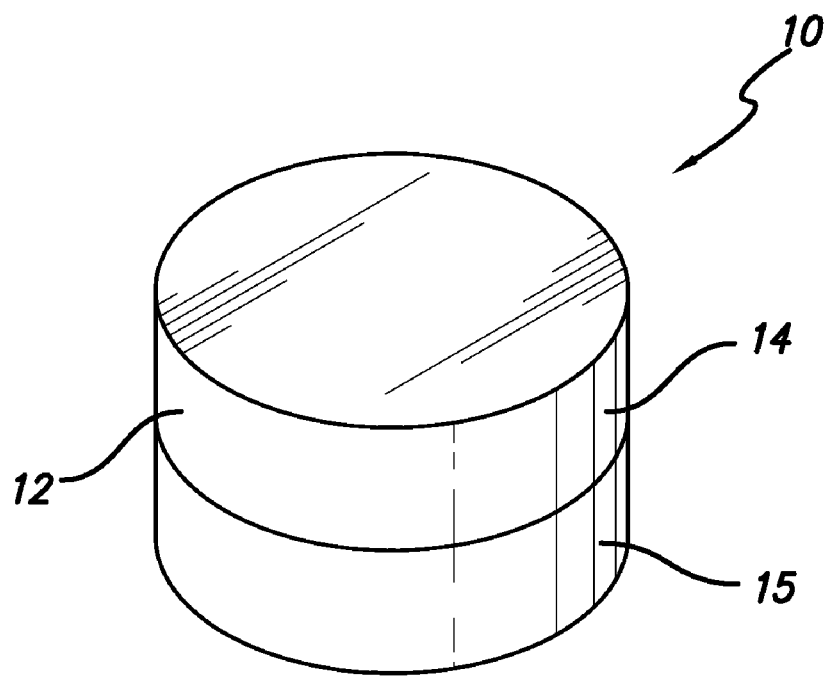
FIG. 1 is schematic view of an ultra-hard polycrystalline construction provided in the form of a compact.

FIG. 1 illustrates an ultra-hard polycrystalline construction 10. The construction comprises a body 12 formed from an ultra-hard polycrystalline material 14, e.g., comprising diamond, polycrystalline diamond (PCD), cubic boron nitride (cBN), polycrystalline cubic boron nitride (PcBN), and mixtures thereof. The body 12 may or may not be attached to a substrate. In the example embodiment illustrated in FIG. 1, the construction is shown to include substrate 15 that is joined together with the body 12 to form a compact.

The substrate may be formed from a variety of different materials such as those useful for forming conventional PCD compacts, like ceramic materials, metallic materials, cermet materials, carbides, nitrides, and mixtures thereof. When the ultra-hard polycrystalline construction comprises polycrystalline diamond a preferred substrate material comprises cemented tungsten carbide (WC—Co).

Figure 2:
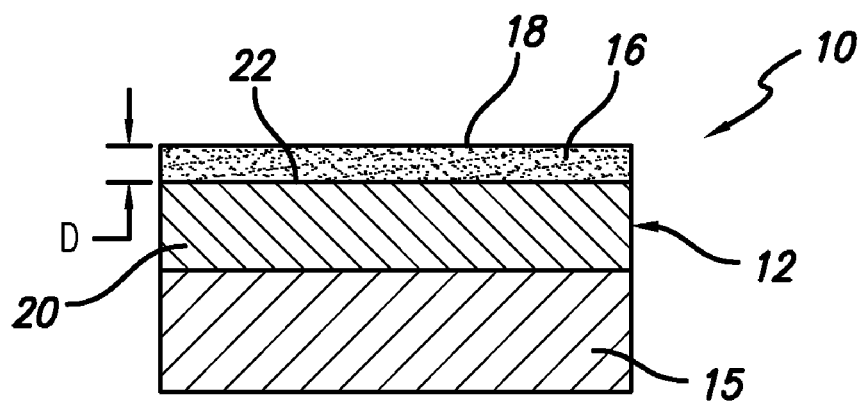
FIG. 2 is a cross-sectional side view of the ultra-hard polycrystalline construction taken along a section of FIG. 1.

FIG. 2 illustrates a cross-sectional view of a section taken through the ultra-hard polycrystalline construction 10 of FIG. 1, which illustrates the material microstructure of the construction and its different regions. In an example embodiment, the body 12 includes a first region 16, that extends a depth "D" into the body from a outside body surface 18, and a second region 20, that extends from the first region 16 to the substrate 15. An interface 22 within the body defines the point of transition between the first and second regions 16 and 20.

In an example embodiment, the body 12 is formed from PCD and the first region 16 includes PCD that has been treated so that it is substantially free of a catalyst material used to form the PCD. As used herein, the term "substantially free" is understood to mean that the catalyst material is removed from the first region, in which case the first region has a material microstructure comprising a polycrystalline diamond matrix phase and a plurality of voids interposed therebetween. The term "substantially free" is also understood to include treatments that render the catalyst material used to form the PCD no longer catalytic, such as by reacting the catalyst material to form a noncatalytic compound and/or by encapsulating the catalyst material with another material that prevents the catalyst material from functioning as a catalyst with the polycrystalline diamond matrix phase.

The catalyst material used to form the PCD in the body can be the same as that used to form conventional PCD by high pressure/high temperature (HPHT) process, such as metals from Group VIII of the Periodic table, with cobalt (Co) being the most common. In an example embodiment, the catalyst material is a solvent metal catalyst such as Ni, Co, Fe, and combinations thereof. The catalyst material can be removed by chemical, electrical, or electrochemical processes. In an example embodiment, the catalyst material is Co and is removed by acid leaching process.

In an example embodiment, it is desired that the depth "D" of the first region within the body be controlled to provide consistent and repeatable characteristics of mechanical and thermal performance for the construction. As explained in greater detail below, it is therefore necessary to develop an accurate and repeatable technique for measuring the depth of the first region in the construction to ensure the consistency of such desired performance characteristics.

The body second region 20 comprises PCD that includes the catalyst material. The PCD region 20 has a material microstructure comprising a polycrystalline diamond matrix and the catalyst material disposed interstitially within the matrix. In an example embodiment, the substrate 15 is attached to the body 12 at the interface with the body second region 20.

The depth of the first region can be controlled by adjusting one or more parameters of the process that are used to treat the first region to render it substantially free of the catalyst material. Once a desired depth is achieved, e.g., to meet the desired performance characteristics for a particular end use application, the process is carefully controlled so that the first region depth in all remaining parts are the same. As noted above, a current method that is used for measuring the depth of the body first region is by destructive testing, whereby the part is cut in half, polished or otherwise prepared, and then is viewed and measured using a scanning electron microscope.

While this technique enables one to determine the depth of the first region with some degree of accuracy, it also results in the destruction of the part, which adversely impacts manufacturing costs and efficiency. Additionally, this process is time consuming as the user typically measures the depth of the first region along the entire part diameter, and then takes the average of the measured points to arrive at the overall part average.

While the use of such destructive testing method is effective for determining the average depth of the first region 16 in the body of the part destroyed, the use of such method on a regular basis is not practical for a large scale manufacturing processes due to both the number of parts destroyed, and the time involved with preparing and measuring each such part. Ideally, it is desired that one be able to measure each and every part that is made for the purpose of ensuring its performance characteristics, rather than depending on a sampling method of testing only one of a number of manufactured parts, which sampling method ultimately relies on the consistency of the manufacturing process to ensure that the remaining unsampled parts conform with the sampled one.

Additionally, the use of such destructive testing technique also enables one to only view the region depth at one location within the part and is not useful in identifying any depth irregularities that may exist along the entire interface between the first and second regions, which depth irregularities (whether patterned or random) may impact the desired performance characteristics of the part.

XRF is a technique that can be used to nondestructively measure the depth of one or more identified regions in the body in a manner that is accurate, and in a manner that provides depth information across the entire region or surface area being measured. XRF relies on bombarding a target material with x-ray energy provided from an x-ray excitation source such as an e-ray tube or a radioactive source. Once the x-ray enters the material it is either absorbed by a target atom or scattered through the material.

When the x-ray is absorbed by a target atom, the atom transfers all of its energy to an innermost electron, which mechanism is referred to as the "photoelectric effect." During this process, if the primary x-ray has sufficient energy, electrons are ejected from the inner shells of the atom, creating vacancies or voids in the vacated shells. These vacancies present an unstable condition for the atom.

Electrons from the atom's outer shells are transferred to the inner shells to return the atom to a stable condition. The process of electron transfer from the outer shell to the inner shell produces a characteristic x-ray having an energy that is the difference between the two binding energies of the corresponding shells. The x-rays emitted by the atom during this process are called X-ray fluorescence (XRF). The process of detecting and analyzing the emitted x-rays is called XRF analysis. Depending on the particular application, XRF can be produced by using not only x-rays but also other primary excitation sources like alpha particles, protons, or high-energy electron beams.

The energy level or wavelength of fluorescent x-rays emitted by the atom is proportional to the atomic number of the target atom and is characteristic for a particular material. The quantity of energy release via such emitted fluorescent x-rays is also dependent upon the thickness or depth of the material being measured.

Figure 3:
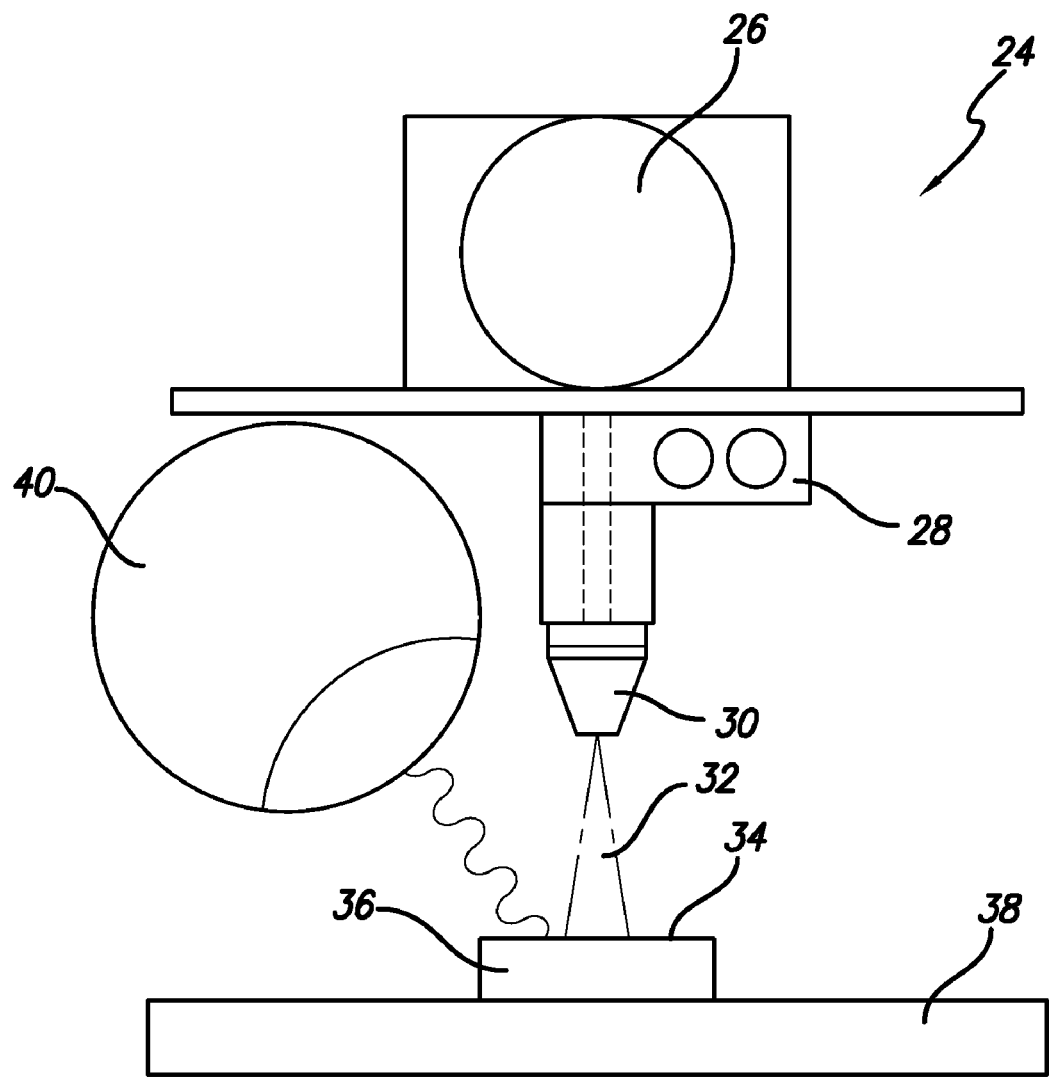
FIG. 3 is a schematic side view of an X-ray fluorescence device useful for determining the thickness and/or variations in thickness of a region within the ultra-hard polycrystalline construction of FIGS. 1 and 2.

FIG. 3 illustrates an XRF device 24 as used to measure the depth of one or more regions in the ultra-hard polycrystalline construction of FIGS. 1 and 2. In an example embodiment, the device 24 comprises an x-ray source 26 and can include a fail-safe shutter 28 and a collimator 30. The collimator is used to direct an incident x-ray 32 onto a desired surface 34 of the ultra-hard polycrystalline construction 36 that is positioned on a suitable positioning assembly 38. In an example embodiment, the positioning assembly and/or the x-ray source can be configured to move if necessary to provide extended coverage over a desired region of the ultra-hard polycrystalline construction 36.

The device 24 further includes a proportional counter 40 that may be part of or separate from the device. The proportional counter may comprise a gas disposed within a counter tube, which gas is ionized by the emission of x-rays or photons from the target material. The emitted x-rays or photons ionize gas in the counter tube that is proportional to their energy, permitting spectrum analysis for determining the nature of the target material and its thickness.

In an example embodiment, the ultra-hard polycrystalline construction 36 is oriented with the device 24 so that the device emits x-ray energy onto the surface 34 of the ultra-hard polycrystalline construction from which the body first region extends. The device is configured having an x-ray source 26 selected to produce x-ray energy that will create a void in the inner shell of the catalyst material that is present in the body second region. In an example embodiment, the catalyst material is cobalt. In the event that the catalyst material in the second region is some other material, the x-ray source is selected to create a void in the inner shell of such other catalyst material.

In an example embodiment, the device is configured to emit x-rays onto a designated surface area of the ultra-hard polycrystalline construction to produce XRF from the targeted atoms, e.g., the catalyst material in the second region, within such designated surface area. X-rays that are generated by the device pass through the ultra-hard polycrystalline construction body first region and to the target atoms in the second region. The XRF emitted from the targeted atoms in the portion of the second region associated with the designated surface area is measured. In an example embodiment, the XRF emitted is an indication of the distance from the surface 34 of the ultra-hard polycrystalline construction to the second region, or the thickness or depth of the first region.

This measured data can be used to generate a plot of the first region thickness within the designated surface area. The device can be used multiple times to emit x-rays onto other surface areas of the ultra-hard polycrystalline construction to obtain desired measurement data and plot the first region thickness or depth a number of different surface areas. Generally speaking, the surface area of the target material that is covered by the device in one instance will vary depending on the size of the collimator. The larger the collimator the larger the surface area being covered, and the fewer number of times that the device will need to be used to generate measurement data sufficient to cover the entire surface area of the target material, if such is desired.

In an example embodiment, it may be desired to use the XRF device to obtain measurement data and plot the first region thickness or depth over the entire surface area of the ultra-hard polycrystalline construction. When used in this manner, the XRF device provides plotted measurement data that produces a topographical view of the interface between the first and second regions within the body.

Such a topographical view can be very helpful in identifying any irregularities along the entire interface, i.e., in the first region thickness or depth, that could possibly be the source of an undesired performance characteristic. Additionally, the use of such a topographical plot can help to identify whether any such irregularities are in a arranged in pattern or are random, which can be useful for the purpose of evaluating and/or controlling the process that is used to form the ultra-hard polycrystalline construction, e.g., to form the body first region.

Figure 4:
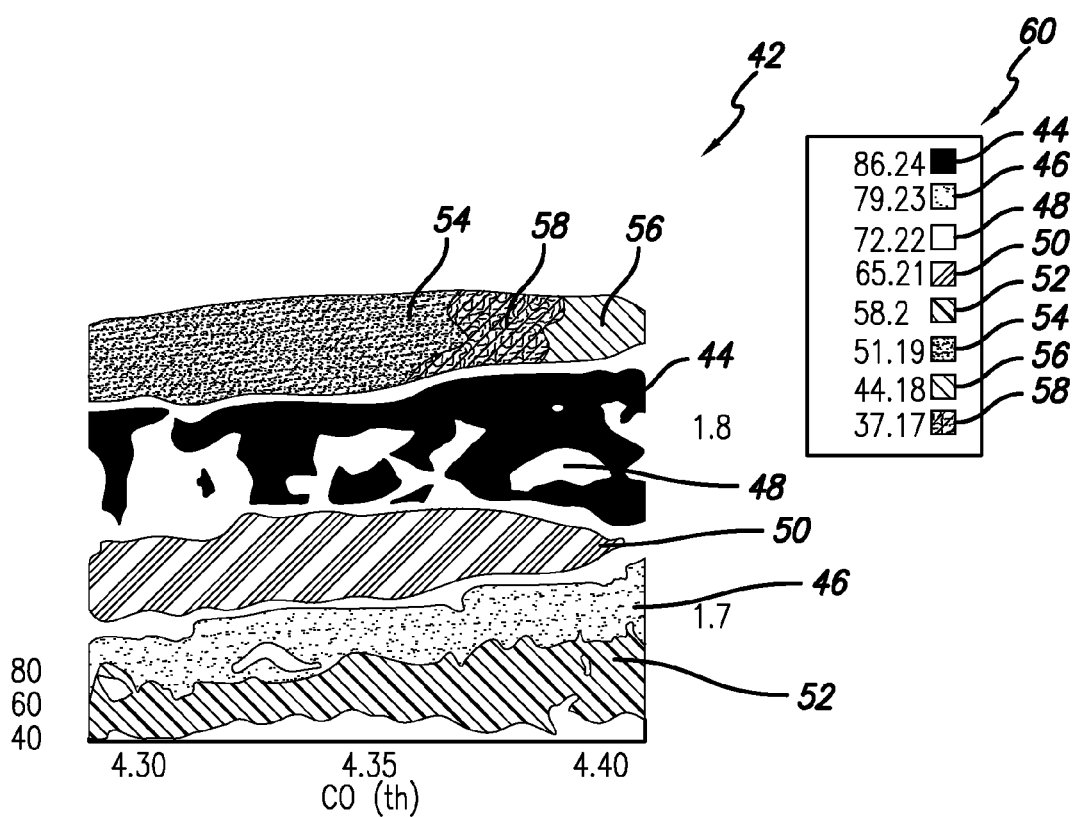
FIG. 4 is a measurement result taken from the X-ray fluorescence device of FIG. 3.

FIG. 4 illustrates a plot 40 that is generated by using the XRF device of FIG. 3. The plot provides a topographical visual indication of the depth along a portion of the body first region (or the distance from the surface of the ultra-hard polycrystalline construction to the second region) within a predetermined surface area. In this example, the XRF device was used to generate a 400 point array scan of a surface area of the ultra-hard polycrystalline construction comprising a body having a polycrystalline diamond matrix first region substantially free of a catalyst material, and a PCD second region that includes a cobalt catalyst material, wherein the target atom is cobalt. The designated surface area had a size of approximately 0.1 by 0.025 inches.

As illustrated in the plot 40, different depths along portion of the first region within this surface area are indicated by differently colored regions 44, 46, 48, 50, 52, 54, 56 and 58. In an example embodiment, a legend 60 is provided to match the colors of the plot to a corresponding numerical thickness. In the example embodiment that is illustrated, the numerical data provided in the legend is provided in dimensions of micrometers.

XRF can be used to nondestructively measure the depth of one or more regions of ultra-hard polycrystalline constructions that are configured for use in a number of different applications, such as tools for mining, cutting, machining and construction applications. Such ultra-hard polycrystalline constructions are particularly well suited for forming working, wear and/or cutting components in machine tools and drill and mining bits such as roller cone rock bits, percussion or hammer bits, diamond bits, and shear cutters.

Figure 5:
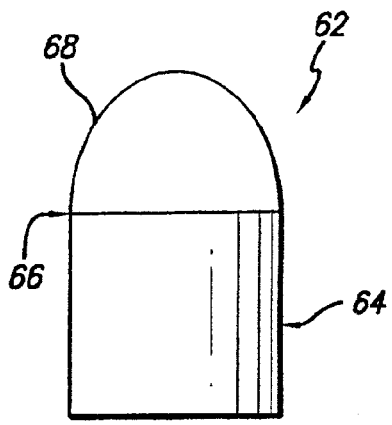
FIG. 5 is a perspective side view of an insert, for use in a roller cone or a hammer drill bit, comprising the ultra-hard polycrystalline construction measured using X-ray fluorescence.

FIG. 5 illustrates an embodiment of an ultra-hard polycrystalline construction, comprising one or more regions within the body that can be measured using XRF, provided in the form of an insert 62 used in a wear or cutting application in a roller cone drill bit or percussion or hammer drill bit. For example, such inserts 62 are constructed having a substrate portion 64, formed from one or more of the substrate materials disclosed above, that is attached to a body 66 having a first and second region as described above. In this particular embodiment, the insert comprises a domed working surface 68, and the thermally stable region is positioned along the working surface and extends a selected depth therefrom into the diamond body. The insert can be pressed or machined into the desired shape or configuration prior to the treatment for rendering the selected region thermally stable. It is to be understood that ultra-hard polycrystalline constructions can be configured as inserts having geometries other than that specifically described above and illustrated in FIG. 5.

Figure 6:
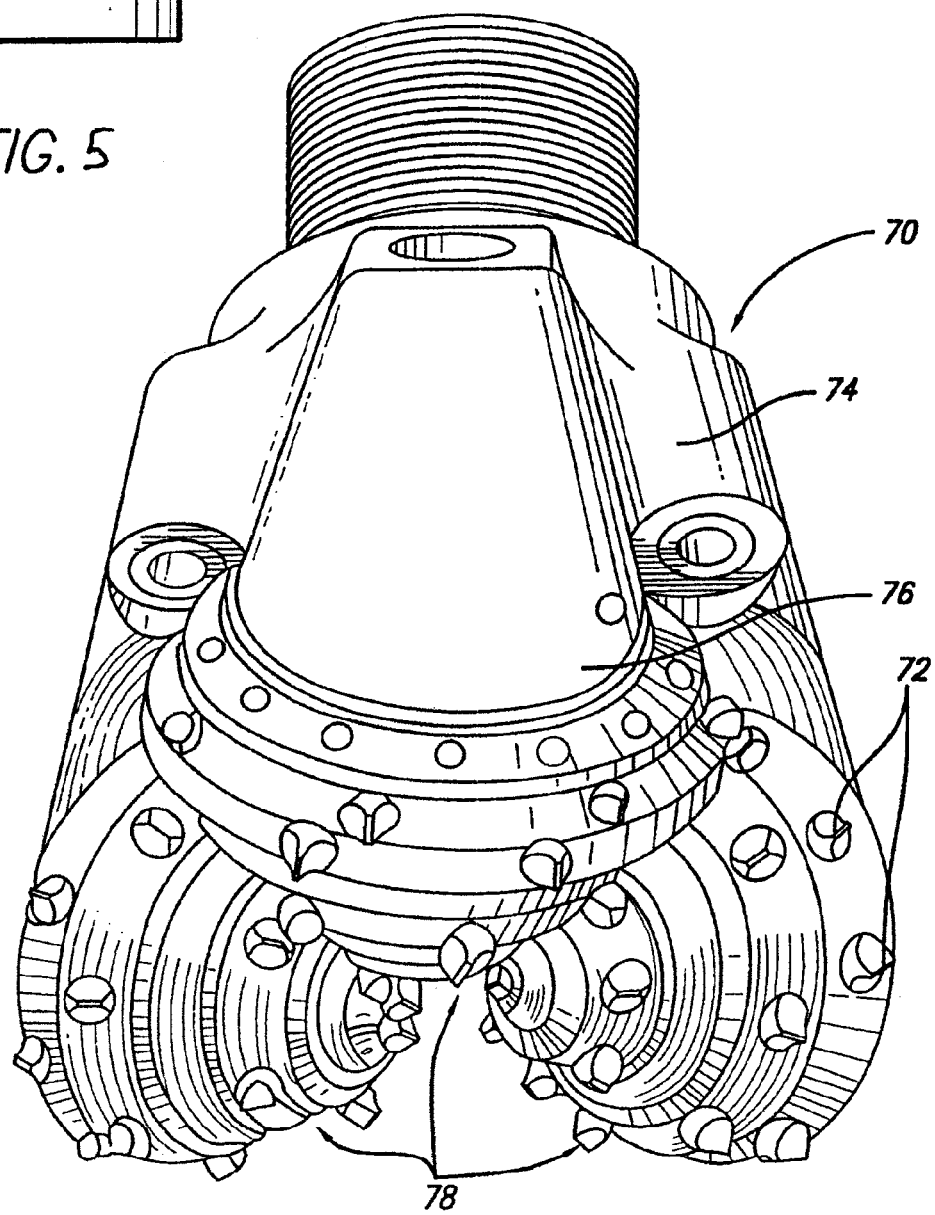
FIG. 6 is a perspective side view of a roller cone drill bit comprising a number of the inserts of FIG. 5.

FIG. 6 illustrates a rotary or roller cone drill bit in the form of a rock bit 70 comprising a number of the wear or cutting inserts 72 disclosed above and illustrated in FIG. 5. The rock bit 70 comprises a body 74 having three legs 76 extending therefrom, and a roller cutter cone 78 mounted on a lower end of each leg. The inserts 72 are the same as those described above comprising the ultra-hard material construction, and are provided in the surfaces of each cutter cone 78 for bearing on a rock formation being drilled.

Figure 7:
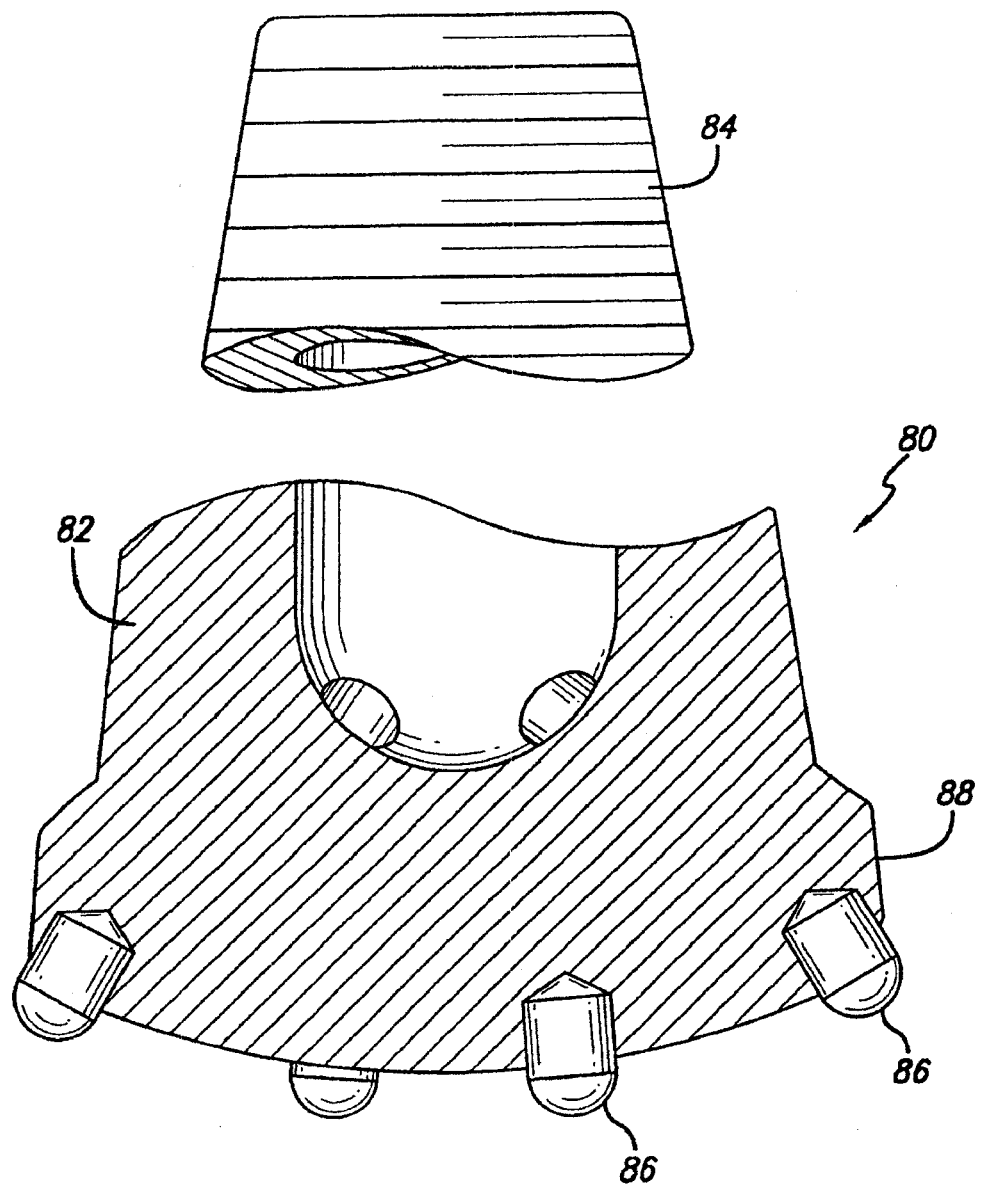
FIG. 7 is a perspective side view of a percussion or hammer bit comprising a number of inserts of FIG. 5.

FIG. 7 illustrates the insert described above and illustrated in FIG. 5 as used with a percussion or hammer bit 80. The hammer bit generally comprises a hollow steel body 82 having a threaded pin 84 on an end of the body for assembling the bit onto a drill string (not shown) for drilling oil wells and the like. A plurality of the inserts 86 are provided in the surface of a head 88 of the body 82 for bearing on the subterranean formation being drilled.

Figure 8:
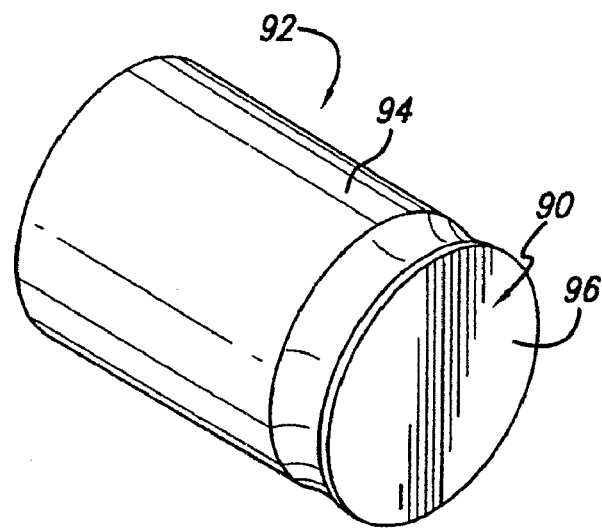
FIG. 8 is a schematic perspective side view of a diamond shear cutter comprising the ultra-hard polycrystalline construction measured using X-ray fluorescence.

FIG. 8 illustrates an ultra-hard polycrystalline construction measured using the XRF method described above as embodied in the form of a shear cutter 90 used, for example, with a drag bit for drilling subterranean formations. The shear cutter 90 comprises a polycrystalline body 92 that is sintered or otherwise attached to a substrate 94. The body 92 includes a working or cutting surface 96 that is formed from the body first region. The working or cutting surface of the shear cutter can extend from the upper surface to a beveled surface (shown as 13 in FIG. 1) defining a circumferential edge of the upper, and the first region of the body can extend a depth from such working surfaces. It is to be understood that ultra-hard polycrystalline constructions can be configured as shear cutters having geometries other than that specifically described above and illustrated in FIG. 8.

Figure 9:
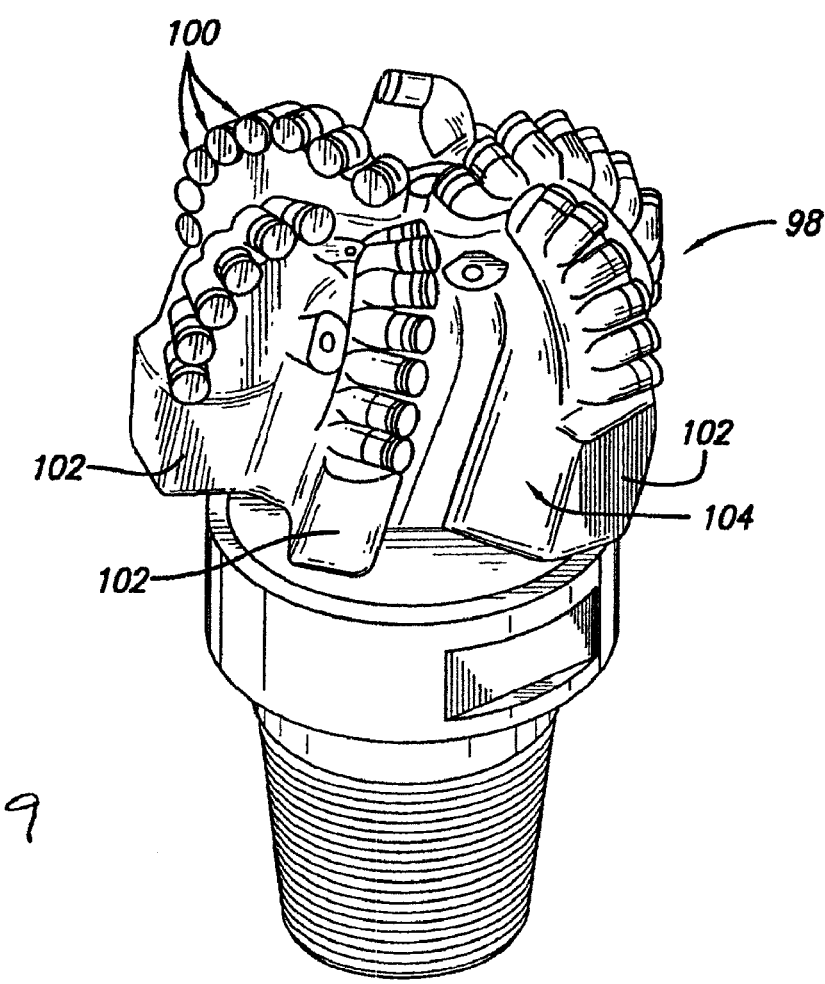
FIG. 9 is a perspective side view of a drag bit comprising a number of the shear cutters of FIG. 8.

FIG. 9 illustrates a drag bit 98 comprising a plurality of the shear cutters 100 described above and illustrated in FIG. 8. The shear cutters are each attached to blades 102 that extend from a head 104 of the drag bit for cutting against the subterranean formation being drilled. Because the shear cutters of this invention include a metallic substrate, they are attached to the blades by conventional method, such as by brazing or welding.

Other modifications and variations of using XRF techniques and methods to measure the thickness or depth of one or more regions within an ultra-hard polycrystalline construc-tions will be apparent to those skilled in the art. It is, therefore, to be understood that within the scope of the appended claims, this invention may be practiced otherwise than as specifically described.

The invention claimed is:

1. A method for nondestructively determining position information of an element disposed within an ultra-hard polycrystalline body comprising a polycrystalline matrix extending continuously throughout, wherein the method comprises the steps of:
   directing x-rays onto a surface of the body, wherein the x-rays are directed through the body, and wherein target atoms in a region of the body emit x-ray fluorescence; and
   receiving the x-ray fluorescence and determining position information of the target atoms within the body.

2. The method as recited in claim 1 further comprising generating a plot of the position within the ultra-hard polycrystalline body.

3. The method as recited in claim 1 comprising directing x-rays onto a number of places on the surface, and receiving each respective x-ray fluorescence.

4. The method as recited in claim 3 wherein the steps of directing and receiving are conducted over an entire surface of the body.

5. The method as recited in claim 1 wherein the polycrystalline matrix in the body comprises diamond.

6. The method as recited in claim 1 wherein the body comprises a catalyst material selected from Group VII materials of the Periodic table.

7. The method as recited in claim 6 wherein the catalyst material comprises the target atoms.

8. The method as recited in claim 6 wherein the catalyst material is cobalt, and cobalt comprises the target atom.

9. The method as recited in claim 1 wherein the ultra-hard polycrystalline body further comprises a substrate attached to the body.

10. The method as recited in claim 1 wherein the ultra-hard polycrystalline body is a cutting insert that is made for attachment with a bit for drilling subterranean formations.

11. The method as recited in claim 1 wherein the ultra-hard polycrystalline body is an insert used in a tooling application.

12. The method as recited in claim 1 wherein the ultra-hard polycrystalline body is an insert used in a wear application.

13. A method for determining a position of a region within a cutting element ultra-hard polycrystalline body, the method comprising the steps of:
   directing x-rays onto at least a surface portion of the polycrystalline body, wherein the polycrystalline body comprises a matrix of bonded together diamond crystals extending throughout the body, wherein the body includes target atoms disposed therein within one or more regions, wherein the x-rays are directed into the body and wherein the target atoms emit x-ray fluorescence; and
   receiving the emitted x-ray fluorescence and determining therefrom a position in the body of the target atoms.

14. The method as recited in claim 13 wherein the determined position of the target atoms defines a region within the body.

15. The method as recited in claim 13 wherein the target atom is a catalyst material, and wherein the catalyst material does not extend throughout the body.

16. The method as recited in claim 15 wherein the catalyst material is selected from Group VIII materials of the Periodic table.

17. The method as recited in claim 13 further comprising directing xrays onto a number of surface portions of the body, receiving a respective x-ray fluorescence emissions, and determining a position from each respective emission.

18. The method as recited in claim 17 further comprising generating a plot of the determined positions as a function of surface location of the ultra-hard polycrystalline body.

19. A bit for drilling subterranean formations comprising a body and a number of blades extending from the body, at least one blade comprising a cutting element having an ultra-hard polycrystalline body with regions having a position as determined according to the method as recited in claim 13.

20. A method for nondestructively obtaining measurement information of target atoms disposed within an ultra-hard polycrystalline construction comprising a polycrystalline matrix phase extending continuously throughout, the method comprising the steps of:
    directing x-ray energy onto a surface of the ultra-hard polycrystalline construction, wherein the x-ray energy passes to the target atoms in the construction to emit fluorescence; and
    receiving the fluorescence and determining the measurement information of the target atoms therefrom.

21. The method as recited in claim 20 wherein the matrix is formed from bonded-together diamond crystals, and wherein the construction comprises a catalyst material, wherein the catalyst material is the target atoms, wherein the target atoms are not disposed continuously throughout the construction, and wherein the measurement information obtained is a position of the target atoms.

22. The method as recited in claim 21 wherein the target atoms are disposed in a the construction.

23. A method for nondestructively examining an ultra-hard polycrystalline construction having a continuous polycrystalline matrix extending therethrough, the method comprising the steps of:
    directing x-ray energy onto a surface of the ultra-hard polycrystalline construction, wherein the x-ray energy passes to one or more target atoms in the construction, and wherein the one or more target atoms emit fluorescence; and
    receiving the fluorescence and from it examining information relating to a position of the target atoms within the construction.

24. A system for nondestructively determining measurement information relating to a region within an ultra-hard polycrystalline construction comprising a polycrystalline matrix extending throughout, the system comprising:
    an emitter that directs a beam of energy in the X-ray spectrum onto a surface of the ultrahard polycrystalline construction and to target atoms disposed within the construction, wherein the target atoms emit fluorescence when contacted by the energy;
    a detector for receiving the fluorescence emitted from the construction; and
    means for determining the measurement information from the fluorescence and providing an indication of the measured information.

25. The system as recited in claim 24 wherein the means for determining provides a visual indication of the measurement information for a region of the construction comprising the target atom.

* * * * *